United States Patent
Chambon et al.

(10) Patent No.: US 9,662,267 B2
(45) Date of Patent: May 30, 2017

(54) SKIN TREATMENT DEVICE EQUIPPED WITH A GUIDE MEANS

(71) Applicant: SEB S.A., Ecully (FR)

(72) Inventors: Vincent Chambon, Soucieu en Jarrest (FR); Martial Maisonneuve, Villefontaine (FR); Xavier Vacheron, Genas (FR)

(73) Assignee: SEB S.A., Ecully (FR)

( * ) Notice: Subject to any disclaimer, the term of this patent is extended or adjusted under 35 U.S.C. 154(b) by 487 days.

(21) Appl. No.: 14/083,518

(22) Filed: Nov. 19, 2013

(65) Prior Publication Data

US 2014/0142471 A1    May 22, 2014

(30) Foreign Application Priority Data

Nov. 19, 2012   (FR) ...................................... 12 60991

(51) Int. Cl.
| | | |
|---|---|---|
| *A61H 15/00* | (2006.01) | |
| *A61H 15/02* | (2006.01) | |
| *A61B 18/20* | (2006.01) | |
| *A61B 18/00* | (2006.01) | |

(52) U.S. Cl.
CPC ............ *A61H 15/00* (2013.01); *A61B 18/203* (2013.01); *A61H 15/02* (2013.01); *A61B 2018/00476* (2013.01); *A61B 2018/00642* (2013.01)

(58) Field of Classification Search
CPC ...... A61H 15/00; A61H 15/02; A61B 18/203; A61B 2018/00476; A61B 2018/00452
See application file for complete search history.

(56) References Cited

U.S. PATENT DOCUMENTS

| 5,486,172 | A | * | 1/1996 | Chess | .................. | A61B 18/203 |
| | | | | | | 206/524.4 |
| 5,766,112 | A | * | 6/1998 | Chuan | .................. | A63B 21/045 |
| | | | | | | 482/121 |
| 6,171,302 | B1 | * | 1/2001 | Talpalriu | .............. | A61B 18/203 |
| | | | | | | 33/706 |
| 6,758,845 | B1 | * | 7/2004 | Weckwerth | .......... | A61B 18/203 |
| | | | | | | 128/898 |
| 2012/0197357 | A1 | * | 8/2012 | Dewey | ................. | A61B 18/203 |
| | | | | | | 607/89 |
| 2012/0283711 | A1 | * | 11/2012 | Liu | ....................... | A61B 18/203 |
| | | | | | | 606/9 |

FOREIGN PATENT DOCUMENTS

| WO | 2006092776 A1 | 9/2006 |
| WO | 2009037641 A1 | 3/2009 |

* cited by examiner

*Primary Examiner* — Justine Yu
*Assistant Examiner* — Kathrynn Lyddane
(74) *Attorney, Agent, or Firm* — The Webb Law Firm

(57) ABSTRACT

The invention relates to a treatment device designed for sequentially treating the skin in a predetermined area via a movement over this area, comprising
 a housing
 a treatment window with a width l and included in a plane
 a guide means adjacent to the treatment window and designed to provide information on the positioning of the device and comprising
 a body attached to the housing, and
 at least one roller having a cylindrical body of which the axis of symmetry Δ is parallel to the plane of the treatment window, the roller being mounted on the body and freely rotating relative to the body.

13 Claims, 5 Drawing Sheets

SKIN TREATMENT DEVICE EQUIPPED WITH A GUIDE MEANS

CROSS-REFERENCE TO RELATED APPLICATION

This application claims priority to French Patent Application No. 1260991 filed Nov. 19, 2012, the disclosure of which is hereby incorporated by reference in its entirety.

FIELD OF THE INVENTION

The present invention relates to the field of treatment devices with a treatment window for treating the skin through this window and a guide means for assisting the user in moving the device over the skin during the treatment so as to obtain an optimum and effective treatment. The invention relates in particular to light source hair removal devices.

DESCRIPTION OF RELATED ART

Hair removal devices using pulsed light are known to the prior art by their function of eliminating hair on the skin and preventing the regrowth thereof. Such a device is equipped with a treatment window often rectangular in shape via which a light emitter sends flashes onto the skin to be treated. In order to treat an entire area, the user must move this window close to the skin from one place to another for making several flashes without leaving visible traces on the skin, since the effect of the treatment is only perceptible a few days or weeks afterwards. As a result the user can easily leave certain portions of the area untreated or repeat the treatment on an already treated portion, which can reduce the efficacy of the treatment or even have adverse consequences for the skin. Hence the need has arisen for a guide means capable of guiding the user in moving the flash window so as to avoid treating a given portion of the skin more than once while at the same time ensuring a thorough treatment on a desired area.

For achieving these objectives, document WO2006092776 describes a device for treating skin with pulsed light comprising a treatment window and an accessory for providing visual or auditory information on the position of the device by means of a position measurement device associated with a control circuit, wherein the measurement device comprises a coded wheel with a circumference corresponding to the width of the treatment window. During the treatment, the user moves the device forward over the skin and causes the wheel to turn; the accessory sends a signal to the user telling him or her to trigger a flash when the measurement device detects an advancement by one turn of the wheel. This solution thus allows an automatic, sequential treatment of an area without having omitted places or places treated several times. Nevertheless the accessory described in this document entails electronic components, thus increasing the cost of the product. In addition it requires a power source, which complicates the use and maintenance of the product.

Also known is a document WO2009/037641, which describes a skin treatment device comprising a treatment window and a guide means attached to the device for guiding the user in moving the device in an intermittent manner. The guide means comprises a roller with a polygonal cross-section defining, on each side, a width corresponding essentially to the width of the treatment window. The user holding the device and moving the window over the skin receives and feels a tactile signal originating from the roller and then knows that he or she must stop moving the device in order to trigger a flash. This document thus proposes an accessory that is entirely mechanical and simple in construction. However, the sensitivity of the human body is not the same among users, and different users may not have the same ability to perceive a tactile signal. This solution might not work for a person who is not sensitive to the tactile signals coming from a roller with a polygonal cross-section. Furthermore, in view of the fact that the shape and dimensions of the roller require great precision in order to meet the functionality requirements of the accessory, the production of the latter is complicated and expensive.

The object of the invention is to remedy the above-mentioned disadvantages and to propose a skin treatment device equipped with a guide means for providing indications that are easier for the user to perceive during the treatment.

Another object of the invention is to provide a skin treatment device equipped with a guide means that permits an easy and smooth movement of the device.

Another object of the invention is to provide a skin treatment device equipped with a low-cost guide means.

Another object of the invention is to provide a skin treatment device equipped with a guide means that is easy to produce.

SUMMARY OF THE INVENTION

Still another object of the invention is to provide a skin treatment device equipped with a guide means that enables an optimum and more effective treatment without omitted or damaged areas.

These objects are achieved with a treatment device designed to treat the skin sequentially in a predetermined area via a movement over this area, comprising a housing, a treatment window of a width l and included in a plane (A), a guide means adjacent to the treatment window for providing indications on the positioning of the device and comprising a body attached to the housing and at least one roller having a cylindrical body of which the axis of symmetry $\Delta$ is parallel to the plane of the treatment window, wherein the roller is mounted on the body and rotates freely relative to the body. According to the invention, the roller has at least one main area and a second area adjacent to and visibly distinct from one another and the body comprises at least one through-opening in relation to the roller, said opening being dimensioned so as to display, in an alternating manner, the main area indicating to the user that the device has reached a desired treatment position and at least a portion of the secondary area indicating to the user that the device is beyond a desired treatment position.

The implementation of the roller makes it possible to guide the user in moving the treatment device in a straight line; hence the movement of the device is more intuitive and smoother. Furthermore, since the visibly distinct and adjacent areas rotate with the movement of the roller, they are alternatingly displayed and viewed on the displacement line by the user through said through-opening in order to indicate the positioning of the device to the user. By said desired treatment position is meant a position in which the treatment window is located right over an untreated surface but essentially adjacent to another surface that has just been treated previously. When the device is in a desired treatment position, the user may be prompted to stop or slow the movement of the device and execute a treatment; if this is not the case the user is prompted to continue moving the device until the device reaches a desired treatment position again.

Additionally, by visibly distinct areas are meant areas with different colors and/or patterns that enable the user to visually distinguish the main area from the secondary area. The user thus easily and quickly perceives the change from one area to another in the through-opening.

Said areas are preferably arranged at least on the bases of the roller. This allows easy viewing of the areas because the bases remain visible whereas the guide curve of the roller is in contact with the skin for the duration of the movement.

On each of its ends the roller advantageously comprises a coded wheel having a tubular body coaxial with the roller and at least one circular face included in the base of the roller, said coded wheel being connected for conjoint rotation with the cylindrical body and removable in translation on the axis Δ. The coded wheels simplify the mounting of the roller on the body as well as the integration of the areas in the roller. The roller can have the shape of a revolving cylinder, which permits the smoothest possible movement over the skin without stops and starts.

[According to a variant, the circular face has in the radial direction three main areas spaced respectively by three secondary areas, the main area having an angular distribution α and the secondary area having an angular distribution β. The number of main and secondary areas was calculated in relation to the dimensions of the roller. By changing the latter, it is possible to increase and decrease the number of areas and also the angular distributions thereof. According to the invention, the size of the roller is adapted ergonomically and to the dimensions of the treatment device. The angular distribution α is dependent on the width of the through-opening and on the circumference of the roller.

[Furthermore, the coded wheel has a circumferential distance of two adjacent areas ranging from 60% to 100% of the width l. This distance preferably corresponds to a value of around 80% of the width l. This represents a travel distance between two adjacent treatments that is slightly smaller than the width l of the treatment window. A small overlap zone between two neighboring treated surfaces is thus created in order to avoid any omitted surface.

In an alternative, the areas are extended from the circular face to the cylindrical body of the roller. This makes it even easier to view the areas.

According to an alternative, the guide means has on said body at least one transparent piece covering at least a portion of said through-opening. The transparent piece can be a glass or plastic lens that gives access to the display of the areas and protects the components of the guide means from dust and impacts.

In its cylindrical body the roller advantageously comprises at least one spring means for moving the coded wheels against the body of the accessory. The installation of the coded wheels is thus facilitated and it is thus possible to keep them as close as possible to the through-openings for facilitating the viewing of the areas.

Furthermore, the cylindrical surface of the roller intended to come into contact with the skin extends slightly beyond the plane A of the treatment window and to the outside. This feature ensures contact between the roller and the skin, even on rounded areas of the human body.

On the surface of its cylindrical body, the roller advantageously comprises means for gripping the skin. By gripping means is meant any use of materials or shapes that increases the coefficient of friction between the roller and the skin for ensuring that the roller turns freely and prevents slipping. Readily conceivable is the use of a material on the surface of the cylindrical body of the roller to render it rough, or even of hemispheres distributed over this surface. The material can be a thermoplastic elastomer-based material (e.g., SEBS, TPE, PP, Epdm, etc.).

Said guide means is preferably detachable from the housing. This gives the user the option of whether to use the guide means or not, or enables the roller and the treatment window to be cleaned more easily between two treatments.

According to the invention, the device comprises a light emitter and a control button for triggering said emission through the window. This gives the user the option of controlling the treatment him/herself.

These objects are also achieved with a process for using the treatment device comprising the following steps: constantly applying the treatment window to the skin and moving the device over the skin, pressing the button when the main area is visible through the through-opening, moving the device forward without pressing the button as long as the secondary area is visible through the through-opening, and repeating the operation over the entire area of skin to be treated. The user follows the course of travel of the device defined by the guide means and repeats these steps until the predetermined area has been completely treated.

The invention will be more clearly understood by studying an embodiment, which is in no way limiting and illustrated in the appended figures. Shown are:

DESCRIPTION OF THE INVENTION

Figure 1:
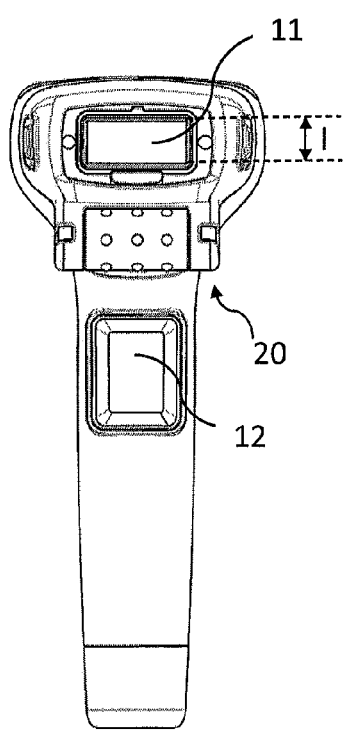
FIG. 1 is a front view of the treatment device and guide means assembly.

A skin treatment device as illustrated in FIG. 1 and designated in its entirety by the reference sign 10 comprises a housing 13 defining a grip area and equipped on the bottom part with a control button 12 for triggering a treatment through a treatment window 11 of a width l when pressed. By treatment device is meant any kind of device for providing a mechanical, optical, or chemical treatment. Alternatively, the pulsed light source used in an optical treatment device can be a LASER, LED, infrared, or other light source. In a specific example, the invention relates to a pulsed light hair removal device designed to inactivate the follicles under the skin in order to remove the hair and prevent or delay its regrowth. During use, the user presses the button 12 to trigger a flash, during which beams of light are directed to the skin through the treatment window 11. To treat a predetermined area such as an arm or leg, the user is prompted to move the device sequentially over the skin and trigger a flash at each desired treatment position defined above.

Figure 2:
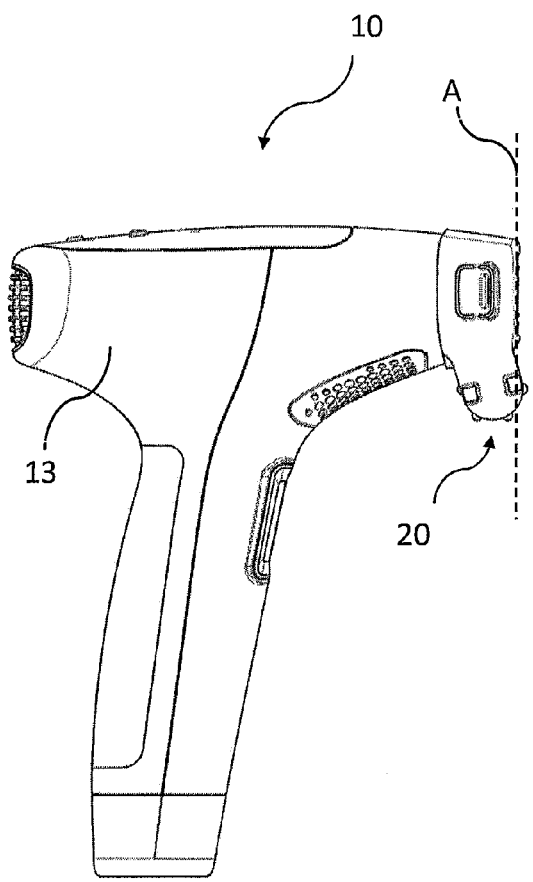
FIG. 2 is a side view of the treatment device and guide means assembly.
Figure 3:
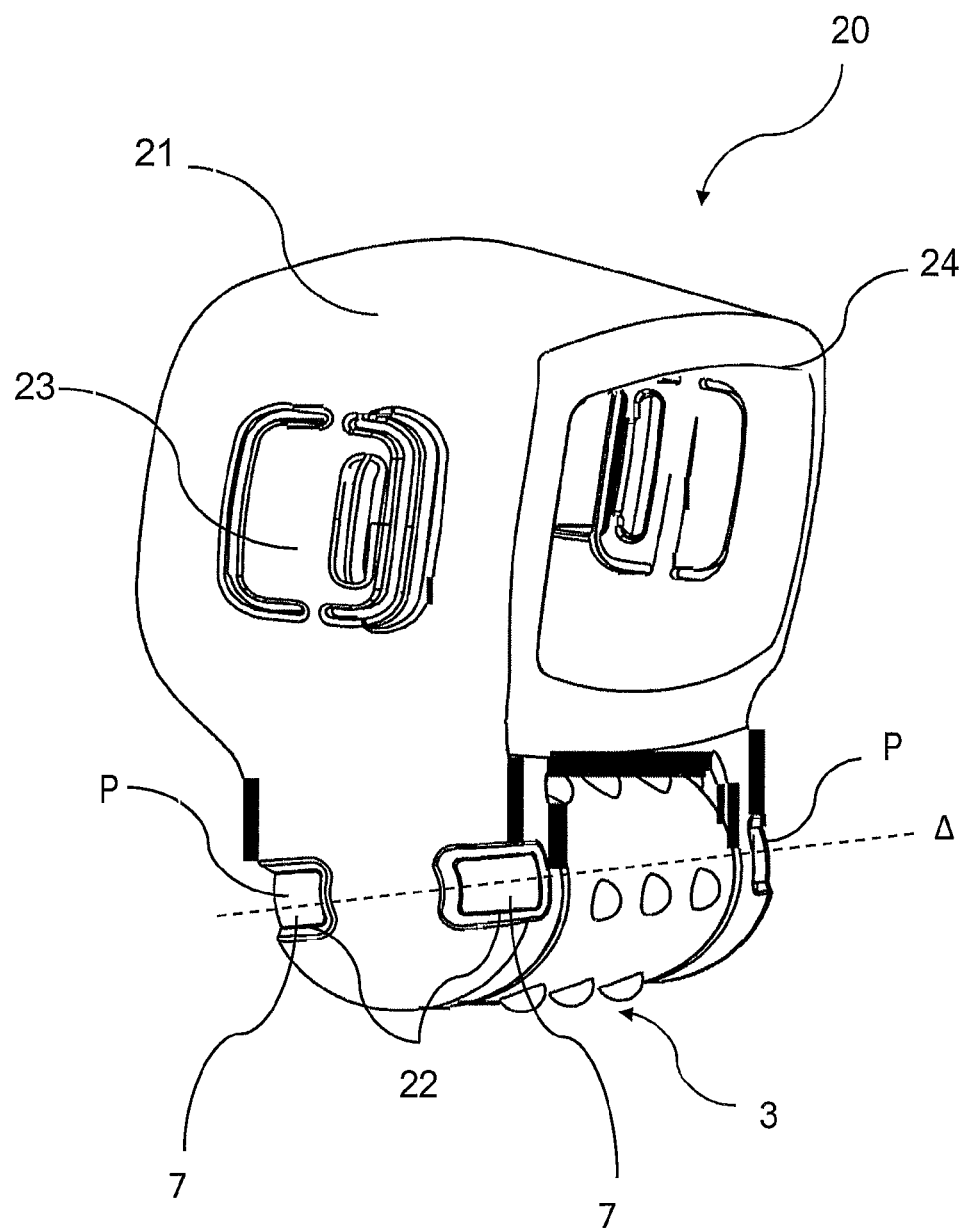
FIG. 3 is a perspective view of the guide means assembly.

As can be discerned in FIGS. 1 and 2 and according to a variant of the invention, the device comprises, on its top part, a guide means 20 in the form of an accessory detachable from the housing of the device, as illustrated in FIG. 3. The accessory 20 comprises a body 21 made of ABS and/or PC with reversible fastening means 23 for hooking onto the housing 13 of the device. The body 21 further comprises an opening 24 which surrounds the treatment window 11 when the accessory 20 is attached to the device, the dimensions of this opening 24 being chosen such that the treatment window 11 is completely exposed by this opening 24. A guide means remaining fixed relative to the housing is obviously conceivable.

On its bottom part, the body 21 comprises a roller 3 with an axis of symmetry Δ mounted on the body and rotating freely relative to the body, the axis Δ being parallel to the plane of the treatment window and perpendicular to the axis of symmetry of the device when the accessory is mounted on the housing. The roller 3 is adjacent to and below the treatment window 11. The roller designed to guide the user in moving the device in a straight line is rotatable in either direction depending on the direction of travel, wherein the width l of the window is on this line of travel. For guiding the user to apply first the roller and then the treatment window in the sequence of travel, it is conceivable for the roller to be rotatable in only one direction of rotation. And lastly, the accessory 20 has through-openings 22 on the body 21, which are arranged in relation to a portion of the roller so as to render the movement of the latter visible through said through-openings 22. In a preferred variant of the invention, the through-openings 22 are located in front of the bases P of the roller 3 so that the movement of the roller is always visible whether the device is held in the left hand or the right hand; the openings are slightly extended by 3 to 5 mm to the front and the back of the accessory in order to widen the viewing field.

Figure 4:
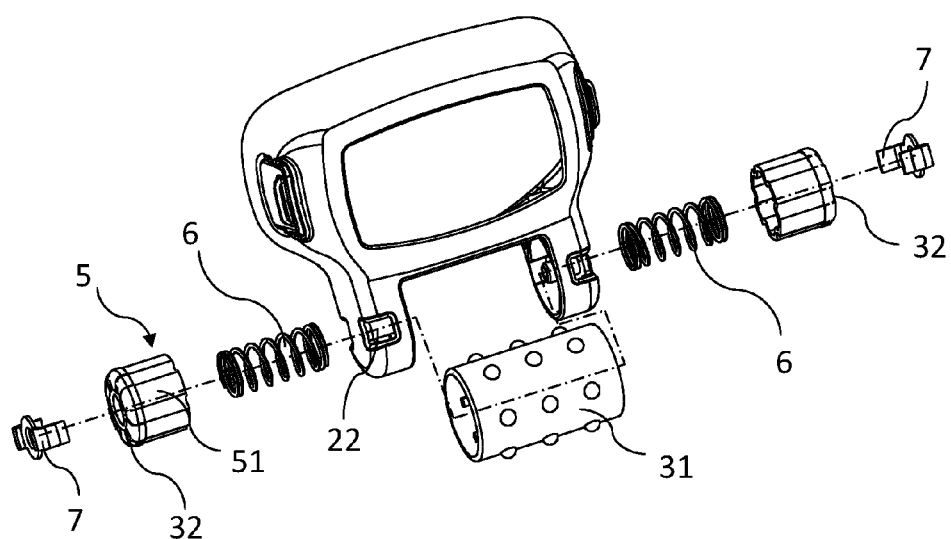
FIG. 4 is a perspective, exploded view of the guide means assembly.

According to a variant and as can be discerned in FIG. 4, on each side of the body 21 the accessory has a transparent piece 7 in the form of a plastic lens revealing both through-openings 22 from the same side.

The roller 3 shall now be described in detail. The roller 3 has the form of a revolving cylinder with two parallel bases P and a cylindrical body 31 with a length of between 20 mm and 60 mm and diameter of between 5 mm and 20 mm. According to an example of the invention, for an optimum result the length and the diameter of the roller are 31 mm and 19.9 mm, respectively. On each of its ends the roller 3 comprises a coded wheel 5 having a tubular body 51 coaxial with the roller 3 and at least one circular face 32 included in the base P of the roller.

Figure 5:
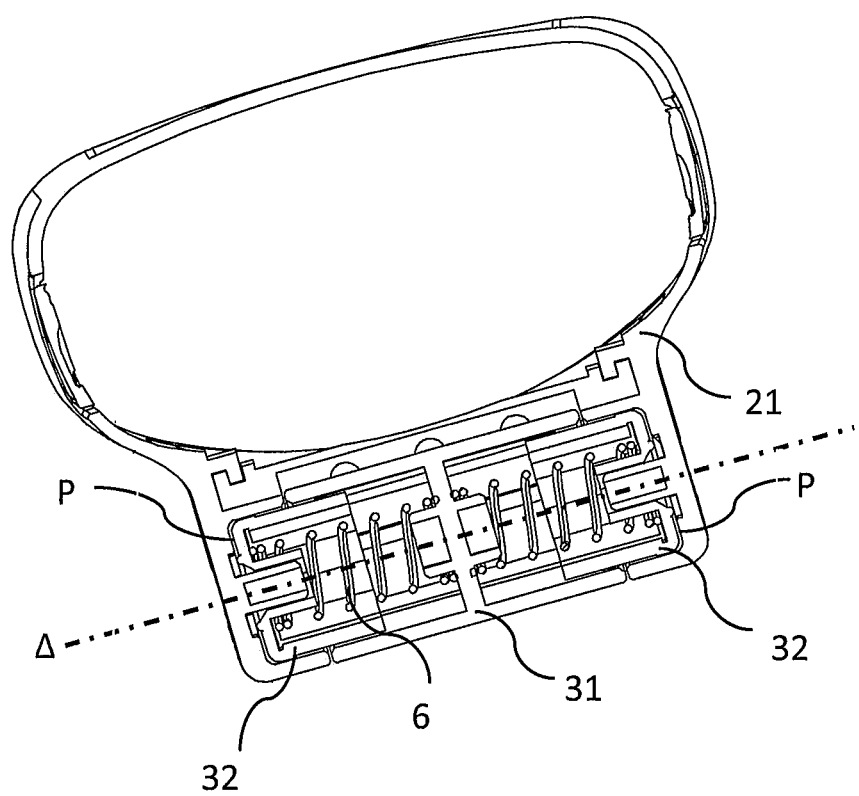
FIG. 5 is a cutaway view of the guide means assembly.
Figure 6:
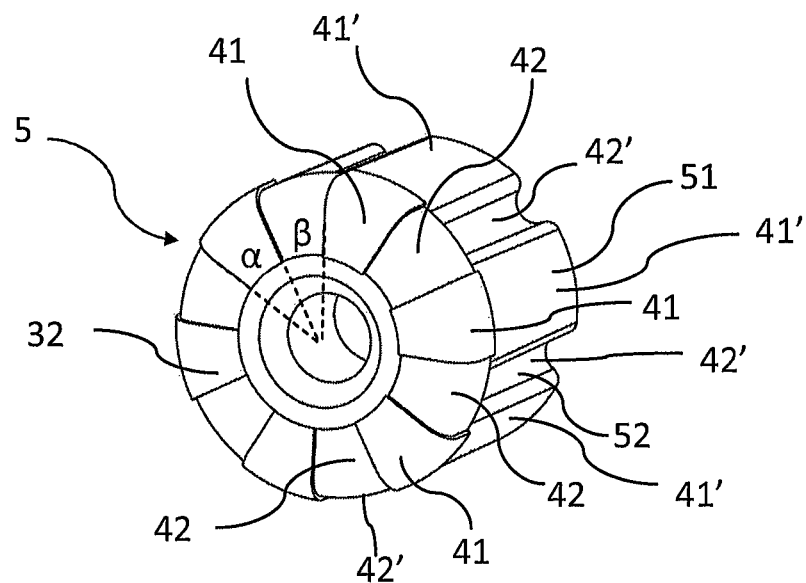
FIG. 6 is a perspective view of the coded wheel.
Figure 7:
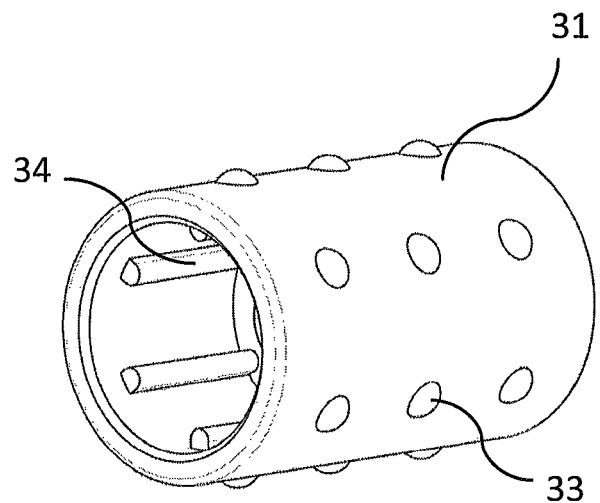
FIG. 7 is a perspective view of the cylindrical body of the roller.

1. As illustrated in FIGS. 6 and 7, the coded wheel 5 has on its tubular body 51 grooves 52 parallel to the axis Δ designed to accommodate raised lines 34 on the inside surface of the cylindrical body 31 of the roller 3 such that the coded wheel and the cylindrical body 31 are connected for conjoint rotation. The circular face 32 of the coded wheel is larger than that of the cylindrical body 31 of the roller and restricts the movement in translation of the coded wheel 5 relative to the cylindrical body 31. As can be discerned in FIG. 5, in its cylindrical body 31 the roller 3 has at least one spring means 6 designed to move the coded wheels 5 against the body 21 of the accessory 20. Thanks to this structure the circular faces 32 can always be kept as close as possible to the through-openings 22. It also permits easy installation of the roller 3 assembly.

As can be discerned in FIG. 6, on its circular face 32 the coded wheel has in the radial direction three main areas 41 each with an angular distribution α, and three secondary areas 42 each with an angular distribution β, both main areas 41 is spaced by a secondary area 42. The purpose thereof is to display the main areas 41, 41' and the secondary areas 42, 42' in the through-opening in an alternating manner. A main area 41 and a secondary area 42 are always adjacent and visibly distinct so that the user can readily observe the changing of the areas in the opening 22. In order to render the main and secondary areas sufficiently distinct, use can be made of color codes such that the two areas 41, 42 have visibly different colors. Use can also be made of surface patterns or finishes on each of the areas 41, 42 as long as both areas 41, 42 are easily and clearly visually distinguishable. In order to widen the visual indication field, the areas 41', 42' can also extend from the circular face 32 to the tubular body 51 so that they are visible from the front and the back of the accessory 20. And lastly, the areas 41, 41', 42, 42' are arranged on the outer surface of the roller 3.

The angular distributions α and β do not have to be identical. Nevertheless it is important that a main area 41 and a neighboring secondary area 42 as a whole have a circumferential distance adapted to the operation of the accessory. So as not to have any surface omitted during the treatment, an overlap of between 0% and 40% of the width l is optionally created on two neighboring treated areas. This value is ideally around 20%. The circumferential distance of two neighboring areas 41 and 42 thus corresponds to essentially 80% of the width l of the window.

During use, the user moves the device over the skin and presses the button when the main area is visible through the opening; the user moves the device forward without pressing the button while the secondary area is visible through the opening and waits until the main area appears again before pressing the button. The user follows the path of travel of the device defined by the guide means and repeats these steps until the predetermined area is completely treated.

Use can also be made of a single-piece roller containing the areas 41, 41', 42, 42' on both bases of the cylindrical body, although this solution is more complicated in terms of manufacturing and mounting on the accessory body.

With the aim of increasing the coefficient of friction of the roller 3 on the skin so that it is easier to move without accidental slipping, the cylindrical body 31 of the roller 3 is made of a flexible material and has on its surface means 33 for gripping the skin in the form of hemispheres.

Obviously other modifications may be made to the invention in the scope of the appended claims.

The invention claimed is:

1. A treatment device for sequentially treating the skin in a predetermined area via a movement over the predetermined area, comprising a housing a treatment window with a width and included in a plane, a guide means adjacent to the treatment window and designed to provide information on the positioning of the device and comprising a body attached to the housing and at least one roller having a cylindrical body of which an axis of symmetry is parallel to the plane of the treatment window, the roller being mounted on the body and freely rotating relative to the body, wherein, the roller has at least one main area and a secondary area adjacent to and visibly distinct from one another, and further wherein the body comprises at least two through-openings in relation to the roller, said openings being dimensioned so as to display in an alternating manner the main area indicating to the user that the device has reached a desired treatment position and at least a portion of the secondary area indicating to the user that the device is beyond a desired treatment position, wherein the at least two through-openings are formed through the body of the guide means and are positioned on opposite sides of the guide means.

2. The device of claim 1, wherein said main area and secondary area are arranged on a base of the roller.

3. The device of claim 2, wherein the roller has on each end a coded wheel having a tubular body coaxial with the roller and at least one circular face included in the base of the roller, said coded wheel being connected for conjoint rotation with the cylindrical body and removable in translation on the axis.

4. The device of claim 3, wherein the at least one main area comprises three main areas on the circular face in a radial direction and the secondary area comprises three secondary areas on the circular face in the radial direction, wherein the three main areas are spaced respectively by the three secondary areas; the three main areas having an angular distribution $\alpha$, the three secondary areas having an angular distribution $\beta$.

5. The device of claim 4, wherein the coded wheel has a circumferential distance of two adjacent areas ranging from 60% to 100% of the width.

6. The device of claim 3, wherein the main and secondary areas are extended from the circular face to the cylindrical body of the roller.

7. The device of claim 1, wherein the guide means has on said body transparent pieces covering at least a portion of said through-openings.

8. The device of claim 3, wherein the cylindrical body of the roller comprises at least one spring means for moving the coded wheels against the body of an accessory.

9. The device of claim 1, wherein the cylindrical surface of the roller intended to come into contact with the skin extends slightly beyond the plane of the treatment window.

10. The device of claim 1, wherein the roller has means for gripping the skin on a surface of the cylindrical body of the roller.

11. The device of claim 1, wherein said guide means is detachable from the housing.

12. The device of claim 1, further including a light emitter and a control button for triggering an emission through the window.

13. A process for using a treatment device for sequentially treating the skin in a predetermined area via a movement over the predetermined area, comprising the following steps:
(a) providing a treatment device, comprising
    a housing
    a treatment window with a width and included in a plane,
    a guide means adjacent to the treatment window and designed to provide information on the positioning of the device and comprising:
        a body attached to the housing; and
        at least one roller having a cylindrical body of which an axis of symmetry is parallel to the plane of the treatment window, the roller being mounted on the body and freely rotating relative to the body, and
    a light emitter and a control button for triggering an emission through the window,
    wherein, the roller has at least one main area and a secondary area adjacent to and visibly distinct from one another, and the body comprises at least two through-openings in relation to the roller, said openings being dimensioned so as to display in an alternating manner the main area indicating to the user that the device has reached a desired treatment position and at least a portion of the secondary area indicating to the user that the device is beyond a desired treatment position, and
    wherein the at least two through-openings are formed through the body of the guide means and are positioned on opposite sides of the guide means,
(b) constantly applying the treatment window on the skin and moving the device on the skin,
(c) pressing the control button when the main area is visible through at least one of the through-openings,
(d) moving the device forward without pressing the button while the secondary area is visible through at least one of the through-openings, and
(e) repeating an operation over an entire area of skin to treat.

* * * * *